United States Patent
Thompson et al.

(10) Patent No.: US 6,451,455 B1
(45) Date of Patent: *Sep. 17, 2002

(54) METAL COMPLEXES BEARING BOTH ELECTRON TRANSPORTING AND HOLE TRANSPORTING MOIETIES

(75) Inventors: Mark Thompson, Anaheim; Yujian You; Andrei Shoustikov, both of Los Angeles, all of CA (US); Paul E. Burrows, Princeton Junction; Stephen R. Forrest, Princeton, both of NJ (US)

(73) Assignees: The Trustees of Princeton University, Princeton, NJ (US); The University of Southern California, Los Angeles, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/053,030

(22) Filed: Apr. 1, 1998

(51) Int. Cl.[7] .............................................. H05B 33/12

(52) U.S. Cl. ..................... 428/690; 428/917; 313/504; 313/506

(58) Field of Search ................... 428/690, 917, 428/704; 313/504, 506

(56) References Cited

U.S. PATENT DOCUMENTS

| | | | |
|---|---|---|---|
| 5,203,974 A | 4/1993 | Kokado et al. | 204/180.2 |
| 5,281,489 A | 1/1994 | Mori et al. | 428/690 |
| 5,294,870 A | 3/1994 | Tang et al. | |
| 5,457,565 A | 10/1995 | Namiki et al. | |
| 5,484,922 A * | 1/1996 | Moore et al. | 546/7 |
| 5,540,999 A | 7/1996 | Yamamoto et al. | 428/411.1 |
| 5,554,220 A | 9/1996 | Forrest et al. | |
| 5,703,436 A | 12/1997 | Forrest et al. | |
| 5,707,745 A | 1/1998 | Forrest et al. | |
| 5,717,289 A | 2/1998 | Tanaka | 313/503 |

FOREIGN PATENT DOCUMENTS

| | | |
|---|---|---|
| EP | 0 704 915 | 4/1996 |
| JP | 5-198378 | * 8/1993 |
| JP | 5-214332 | * 8/1993 |
| JP | 10-219241 | * 8/1998 |

OTHER PUBLICATIONS

Steven L. Murov, et al., "Handbook of Photochemistry", 1993, pp. 260–278. (No Month).

Berggren, M., et al., Light Amplification in Organic Thin Films Using Cascade Energy Transfer, *Nature* 389, pp 466–496, Oct. 1997.

Kalinowski, J., et al., "Electroabsorption Study of Excited States in Hydrogen–bonding Solids: Epindolidione and Linear Trans–quinacridone," *Chem. Phys.* 182, (1994), pp. 341–352. (No Month).

D. Kim, et al., "Synthesis of Electroluminescent Polymer Containing Charge Transport and Emissive Chromophores on Polymer Skelton", *Chemistry Letters*, pp. 587–588, (1995). (No Month).

(List continued on next page.)

*Primary Examiner*—Marie Yamnitzky
(74) *Attorney, Agent, or Firm*—Kenyon & Kenyon

(57) ABSTRACT

An organic light emitting device comprising a heterostructure for producing electro-luminescence. The heterostructure has a charge carrier layer that includes a compound having molecules having at least one electron transporting moiety that is a 2-methyl-8-quinolinolato ligand coordinated with a metal chosen from the group Al, Ga, and In, and at least one hole transporting moiety. For example, the compound may be bis(2-methyl-8-quinolinolato)[p-(N-phenyl-2-naphthylamino)phenolato]aluminum(III), bis(2-methyl-g-quinolinolato)p-carbazolphenolato)aluminum(III), or bis(2-methyl-8-quinolinolato)(m-carbazolphenolato)aluminum (III).

17 Claims, 7 Drawing Sheets

Absorption and Fluorescent Spectra of Al-pNP, Al-pCb, and Al-mCb in $CH_2Cl_2$ Solution

OTHER PUBLICATIONS

Kim, H.H., et al., "Silicon Compatible Organic Light Emitting Diode", *Journal of Lightwave Technology*, vol. 12, No. 12, pp. 2107–2113 (Dec. 1994).

Martin, M., et al., "Ultrafast Intramolecular Charge Transfer in the Merocyanine Dye DCM," *Chem. Phys.* 192, (1995), pp. 367–377. (No Month).

Tang, C.W., et al., "Electroluminescence of Doped Organic Thin Films," *J. Appl. Phys.* 65 (9), pp. 3610–3616, May 1989.

Garbuzov, D.Z., et al., *Chem. Phys. Lett*, 249, pp. 433–437, Feb. 1996.

Kido, J., et al. *Appl. Phys. Lett.*, 65, (17), pp. 2124–2126, Oct. 1994.

Kido, J., et al., *J. Alloys and Compounds*, 192, (1993), pp. 30–33. (No Month).

Kijima, Y., et al., *IEEE Transactions on Electron Devices*, 44, (8), pp. 1222–1228, Aug. 1997.

Littman, J., et al., *J. Appl. Phys.*, 72, (5), pp. 1957–1960, Sep. 1992.

Sano, T., et al., *Japan J. Appl. Phys*, 34, pp. 1883–1887, Apr. 1995.

Schmidbaur, H., et al., *Z. Naturforsch*, B. 46, 901 (1991) (abstract only). (No Month).

Shen, Z., et al., *Science*, 276, pp. 2009–2011, Jun. 1997.

Tasch, S., et al., *Adv. Mater.*, (1), pp. 33–36, Jan. 1997.

Tsutsui. T., et al., *Appl. Phys. Lett.*, 65, (15), pp. 1868–1870, Oct. 1994.

Forrest, et al., "Organic emitters promise a new generation of displays," Feb. 1995 Laser Focus World, pp. 99–107.

Tamoto, et al., "Electroluminescence of 1,3,4–Oxadiazole and Triphenylamine–Containing Molecules as an Emitter in Organic Multilayer Light Emitting Diodes," 1997 pp. 1077–1085, Chem. Mater. vol. 9, No. 5, (No Month).

Tang, et al., "Organic electroluminescent diodes," Appl. Phys. Lett 51 (12), Sep. 21, 1987 pp. 913–915.

Tsutsui, et al., "Synthesis of Electroluminescent Polymer Containing Charge Transport and Emissive Chromophores on Polymer Skeleton," *Chemistry Letters* (1995), p. 587. No Month.

Bulovic et al., "Transparent Light–emitting Devices", Nature 380, p. 29, Mar. 1996.

Whitlock et al., "Investigations of Materials and Device Structures for Organic Semiconductor Solar Cells", Optical Eng., vol. 32., No. 8, 1921–1934 (Aug. 1993).

\* cited by examiner

Figure 1. Absorption and Fluorescent Spectra of Al-pNP, Al-pCb, and Al-mCb in $CH_2Cl_2$ Solution Figure 2. EL and PL of Al-pNP devices.

METAL COMPLEXES BEARING BOTH ELECTRON TRANSPORTING AND HOLE TRANSPORTING MOIETIES

GOVERNMENT RIGHTS

This invention was made with Government support under Contact No. F33615-941-1414 awarded by DARPA. The government has certain rights in this invention.

FIELD OF INVENTION

The present invention is directed to an organic light emitting device having a charge carrier layer. In particular, the charge carrier layer contains a compound having molecules that have at least one electron transporting moiety and at least one hole transporting moiety.

BACKGROUND OF THE INVENTION

Organic light emitting devices (OLEDS) are comprised of several organic layers in which one of the layers is comprised of an organic material that can be made to electroluminesce by applying a voltage across the device. C. W. Tang et al., Appl. Phys. Lett. 51, 913 (1987). Certain OLEDs have been shown to have sufficient brightness, range of color and operating lifetimes for use as a practical alternative technology to LCD-based full color flat-panel displays. S. R. Forrest, P. E. Burrows and M. E. Thompson, Laser Focus World, February, 1995. Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), which represents a significant step toward realizing high resolution, independently addressable stacked R-G-B pixels, was reported in U.S. Pat. No. 5,703,436, Forrest et al. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag-ITO electrode layer for electron-injection. A device was disclosed in which the ITO side of the Mg—Ag-ITO electrode layer was used as a hole-injecting contact for a second, different color-emitting OLED stacked on top of the TOLED. Each layer in the stacked OLED (SOLED) was independently addressable and emitted its own characteristic color, red or blue. This colored emission could be transmitted through the adjacently stacked transparent, independently addressable, organic layer, the transparent contacts and the glass substrate, thus allowing the device to emit any color that could be produced by varying the relative output of the red and blue color-emitting layers.

U.S. Pat. No. 5,703,745, Forrest et al, disclosed an integrated SOLED for which both intensity and color could be independently varied and controlled with external power supplies in a color tunable display device. U.S. Pat. No. 5,703,745, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers between an anode and a cathode. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the HTL, while the cathode injects electrons into the ETL. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. These excitons are trapped in the material which has the lowest energy. Recombination of the short-lived excitons may be visualized as an electron dropping from its conduction potential to a valence band, with relaxation occurring, under certain conditions, preferentially via a photoemissive mechanism.

The materials that function as the ETL or HTL of an OLED may also serve as the medium in which exciton formation and electro-luminescent emission occur. Such OLEDs are referred to as having a "single heterostructure" (SH). Alternatively, the electro-luminescent material may be present in a separate emissive layer between the HTL and the ETL in what is referred to as a "double heterostructure" (DH).

In a single heterostructure OLED, either holes are injected from the HTL into the ETL where they combine with electrons to form excitons, or electrons are injected from the ETL into the HTL where they combine with holes to form excitons. Because excitons are trapped in the material having the lowest energy gap, and commonly used ETL materials generally have smaller energy gaps than commonly used HTL materials, the emissive layer of a single heterostructure device is typically the ETL. In such an OLED, the materials used for the ETL and HTL should be chosen such that holes can be injected efficiently from the HTL into the ETL. Also, the best OLEDs are believed to have good energy level alignment between the highest occupied molecular orbital (HOMO) levels of the HTL and ETL materials.

In a double heterostructure OLED, holes are injected from the HTL and electrons are injected from the ETL into the separate emissive layer, where the holes and electrons combine to form excitons.

Various compounds have been used as HTL materials or ETL materials. HTL materials mostly consist of triaryl amines in various forms which show high hole mobilities ($\sim 10^{-3}$ $cm^2$ Vs). There is somewhat more variety in the ETLs used in OLEDs. Aluminum tris(8-hydroxyquinolate) ($Alq_3$) is the most common ETL material, and others include oxidiazol, triazol, and triazine.

For example, a typical single heterostructure device may be made of ITO/TPD/$Alq_3$/Mg—Ag. ITO serves as the anode, N,N'-diphenyl-N,N'-bis(3-methylphenyl)-1,1'biphenyl-4,4'diamine (TPD) serves as the HTL, $Alq_3$ serves as the ETL, and Mg—Ag serves as the cathode. When a bias is applied across the device, holes are injected from ITO into TPD and migrate to the interface between the TPD and the $Alq_3$, and electrons are injected from the Mg—Ag alloy into $Alq_3$ and move to the same interface. Holes are injected from the TPD into the $Alq_3$, where they combine with electrons to form excitons. The excitons randomly diffuse through the $Alq_3$ layer until they recombine, preferentially via a photoemissive mechanism. The maximum distance of exciton migration in the $Alq_3$ layer of such a device is estimated to be around 300 Å in $Alq_3$.

Most emissive materials used in OLEDs have either low hole mobility or low electron mobility. As a result, exciton formation typically occurs very close to the interface where the charge carrier having the lower mobility is injected into the emissive layer. For example, most ETL materials have very poor hole conducting properties, such that the excitons will be preferentially formed very close to the HTL/ETL interface in a single heterostructure OLED having an emissive ETL. Because excitons are very short lived, they do not move very far before recombining. As a result, only a small volume of the ETL is used for exciton formation and recombinations. Using only a small volume of the emissive layer for exciton formation and recombination may lead to lower lifetime for the OLED. There is therefore a need for an emissive layer having a high electron mobility and a high hole mobility, such that exciton formation can occur in a reasonable volume of the layer. For example, there is a need for an ETL having a high hole mobility, so that exciton formation and light emission can occur in a reasonable volume of the ETL of a single heterostructure OLED having an emissive ETL.

It was first thought that mixing HTL and ETL materials together would decrease the spatial separation and increase the diffusion of holes into the ETL material. This idea was first demonstrated in a variety of polymer systems where both hole transporting and electron transporting moieties were blended into the polymer matrix. The most commonly used combination is the PVK/PBD system where PVK (polyvinylcarbazole) serves as hole transporter and PBD (2-(4-t-butylphenyl)-5-(4-phenyl-1-phenylene)oxidiazole) as the electron transporter. A number of different dyes have been doped into this system as emitting centers to generate colors from blue to red.

U.S. Pat. No. 5,294,870 discloses a series of aluminum (III) complexes with two 8-hydroxyquinaldine ligands and a derivative of phenolate ligand, $Alq'_2(OAr)$. All of these species are blue emitters and are reasonable electron transporters. Devices have been fabricated with $Alq'_2(OAr)$ sandwiched between TPD and $Alq_3$. This configuration is necessary because of the poor electron injection from the Mg—Ag electrode. Nevertheless, these devices show blue-green emissions in their electro-luminescent (EL) spectra and are nearly identical to their photo-luminescent (PL) spectra. These compounds have also shown good properties as host materials for doping with other fluorescent dyes, such as perylene to give blue emission. However, the ETL materials disclosed are poor hole transporters.

At the molecular level, Tamoto et al have designed a series of new emitting materials having an oxadiazole group as electron transporter and a triphenylamine as hole transporter. Tamoto et al, Electroluminescence of 1,3,4-Oxadiazole and Triphenylamine-Containing Molecules as an Emitter in Organic Multilayer Light Emitting Diodes, Chem. Mater. 9, 1077–1085 (1997). Layers formed of these emitting materials tend to form exciplexes with hole transporters with low ionization potentials. When exciplexes are not formed, high external quantum efficiency and energy conversion efficiency are observed. However, devices consisting of these materials suffer from low luminescent lifetimes. It was also discovered that these emitting materials have more tendency to transfer electrons than holes.

SUMMARY OF THE INVENTION

The present invention is directed to an organic light emitting device (OLED) comprising a heterostructure for producing electro-luminescence. The heterostructure has a charge carrier layer that includes a compound having molecules having at least one electron transporting moiety and at least one hole transporting moiety wherein the electron transporting moiety is a 2-methyl-8-quinolinolato ligand coordinated with a Group III metal, such as Al, Ga, or In. The hole transporting moiety may be a hole transporting amine moiety. One example of such a hole transporting amine moiety is a triarylamine derivatized phenoxide. The compound may therefore have, for example, two 2-methyl-8-quinolinolato ligands coordinated with Al as electron transporting moieties and one triarylamine derivatized phenoxide as a hole transporting moiety.

The charge carrier layer that includes a compound having molecules having at least one electron transporting moiety and at least one hole transporting moiety may be an emissive layer, such as the ETL of a single heterostructure, or the separate emissive layer of a double heterostructure. This compound may also be used as an injection enhancement layer, such as an electron injection enhancement layer, which is disposed between the ETL and cathode of an OLED, and enhances the injection of electrons from the cathode into the ETL, or a hole injection enhancement layer, which is disposed between the HTL and anode of an OLED, and enhances the injection of holes from the anode into the HTL.

The present invention further provides an ETL having a high hole mobility, so that holes can be transported away from the HTL/ETL interface of a single heterostructure to ultimately recombine with electrons throughout a large volume of the ETL. It is believed that this feature enhances the lifetime of OLEDs.

Further objectives and advantages of the present invention will be apparent to those skilled in the art from the detailed description of the disclosed invention. (

DETAILED DESCRIPTION

Figure 1:
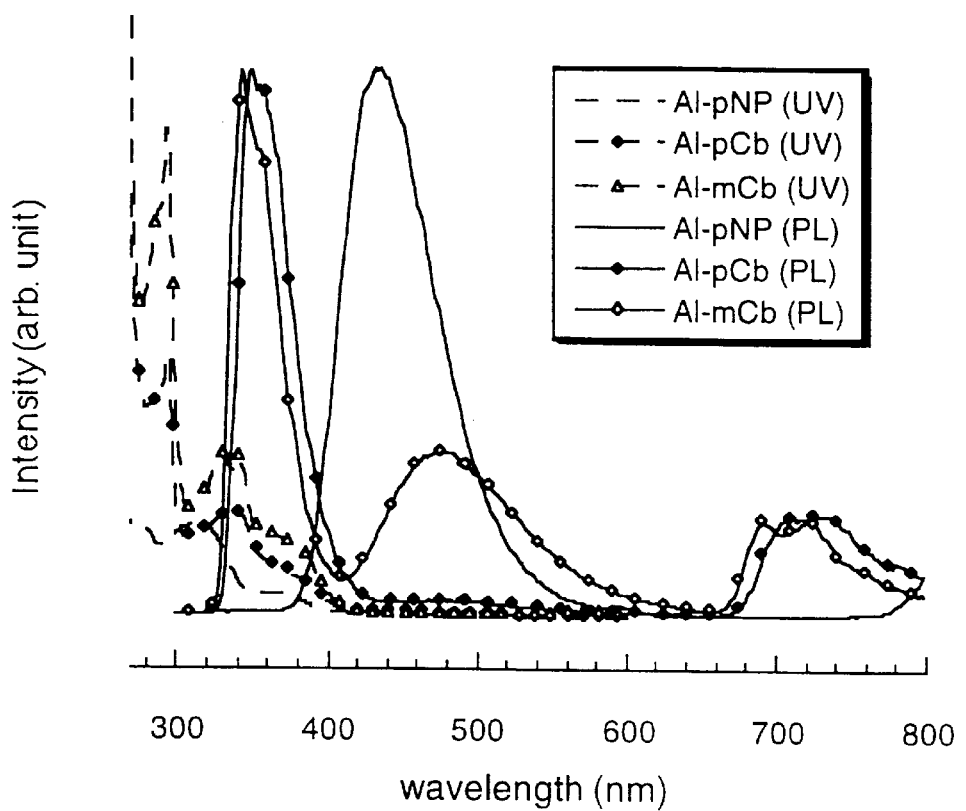
FIG. 1 shows absorption and fluorescent spectra of Al-pNP, Al-pCb, and Al-mCb in a $CH_2Cl_2$ solution.

The present invention will now be described in detail for specific preferred embodiments of the invention, it being understood that these embodiments are intended only as illustrative examples and the invention is not to be limited thereto.

The present invention is directed to an organic light emitting device (OLED) comprising a heterostructure for producing electro-luminescence. In particular, the heterostructure has a charge carrier layer that includes a compound having molecules having at least one electron transporting moiety and at least one hole transporting moiety wherein the electron transporting moiety is a 2-methyl-8-quinolinolato ligand coordinated with a Group III metal, such as Al, Ga, or In. The hole transporting moiety may be a hole transporting amine moiety.

As used herein, the term "charge carrier layer" may refer to a "hole transporting layer" (HTL,) an "electron transporting layer" (ETL) or, for an OLED having a double heterostructure (DH), a "separate emissive layer." The charge carrier layer that includes a compound having molecules having at least one electron transporting moiety and at least one hole transporting moiety may be an emissive layer, such as the ETL of a single heterostructure (SH), or the separate emissive layer of a double heterostructure. The charge carrier layer that includes a compound having molecules having at least one electron transporting moiety and at least one hole transporting moiety may also be a non-emissive layer, such as an electron injection enhancement layer disposed between the cathode and ETL of an OLED.

The term "hole transporting moiety" as used herein, refers to a group which, when present in a material contained in a layer of an OLED, causes the material to provide electrical conduction through the layer, when a voltage is applied, by conduction of holes. The term "electron transporting moiety" as used herein, refers to a group which, when present in a material contained in a layer of an OLED, causes the material to provide electrical conduction through the layer, when a voltage is applied, by conduction of electrons. The term "hole transporting amine moiety" as used herein, refers to an amine group that is a hole transporting moiety. Such hole transporting amine moieties are typically comprised of nitrogen atoms that are directly bonded to two phenyl groups (in addition to a phenyl group that forms the ligand bond with the Group III metal), wherein the two phenyl groups may be joined so as to form a heterocyclic ring including the nitrogen, for example, a carbazole group, or the two phenyl groups may be unattached to each other. Each phenyl group may itself be fused with still another phenyl group, being bonded to the nitrogen atom, for example, either as a 1-naphthyl group or as a 2-naphthyl group.

In particular, the present invention is directed to a compound having the chemical structure:

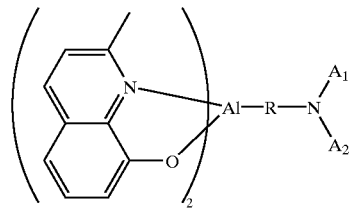

wherein $A_1$ and $A_2$ are each comprised of one or more phenyl groups that produce an overall hole transporting functionality, and —R— is an alkyl or aryl group, preferably an aryl group, that is capable of forming a ligand bond with a Group III metal. The phenyl groups of $A_1$ and $A_2$ may be joined so as to form a heterocyclic ring including the nitrogen, e.g., so as to constitute a carbazole group, or the phenyl groups of $A_1$ and $A_2$ may be unattached to each other. Each phenyl group may itself be fused with still another phenyl group and bonded to the nitrogen atom either, for example, as a 1-naphthyl group or as a 2-naphthyl group. The —R— group may be a hole transporting substituting alkoxide, thiolate, benzoic acid or chelating oxygen or nitrogen group (such as substituted acetylacetonate). Preferably, the R-group is a p-amino-substituted phenoxide group. Another Group III metal, such as Ga or In, may be substituted for the Al.

The 2-methyl-8-quinolinolato ligand coordinated with a Group III metal, such as Al, acts as an electron transporting moiety. The amine group acts as a hole transporting moiety. Because the molecule has both electron and hole transporting moieties, a charge carrier layer made from the molecule will have a high electron mobility and a high hole mobility. Using such a charge carrier layer as the ETL of a single heterostructure, for example, allows holes to move a substantial distance into the ETL before recombining with an electron to form an exciton. As a result, the luminescent region of such an ETL is larger than the luminescent region of an ETL having a low hole mobility. This larger electro-luminescent region may result in a longer electro-luminescent lifetime. Similarly, using such a charge carrier layer as a separate emissive layer of a double heterostructure leads to a luminescent region larger than that of a separate emissive layer having a lower hole or electron mobility, and a longer electro-luminescent lifetime.

In particular, the compound having molecules having at least one electron transporting moiety and at least one hole transporting moiety may be bis(2-methyl-8-quinolinolato) [p-(N-phenyl-2-naphthylamino)phenolato]aluminum(III), which is referred to as Al-pNP, bis(2-methyl-8-quinolinolato)(p-carbazolphenolato)aluminum(III), which is referred to as Al-pCb, or bis(2-methyl-8-quinolinolato)(m-carbazolphenolato)aluminum(III), which is referred to as Al-mCb:

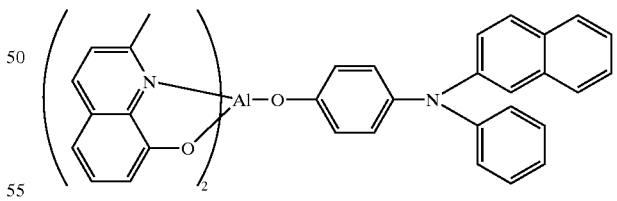

Al-pNP

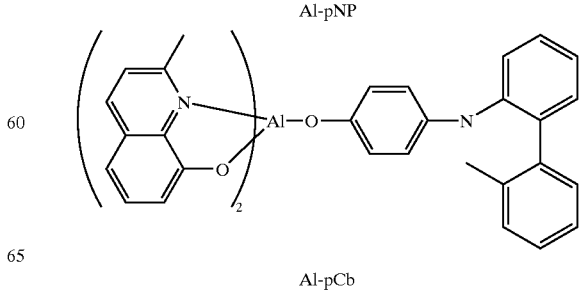

Al-pCb

-continued

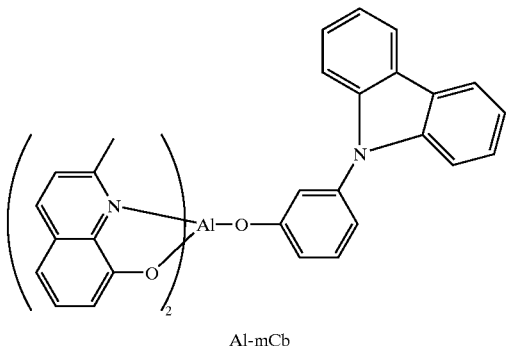

Al-mCb

Experimental results show that solid films of Al-pCb have a photo-luminescent emission about 100 times more efficient than that of Al-pNP. This difference may be explained by the different structure of the two molecules. In particular, Al-pCb has a more rigid conformation due to its carbazol moiety, which may prevent the molecules in the solid state from non-radiative self-quenching, which could account for the hundred times greater efficiency of the photo-luminescent emission of Al-pCb as compared to Al-pNP.

The OLEDs of the present invention are comprised of a heterostructure for producing electro-luminescence which may be fabricated as a single heterostructure or as a double heterostructure. As used herein, the term "heterostructure for producing electro-luminescence" refers to a heterostructure that includes for a single heterostructure, for example, a substrate, a hole injecting anode layer in contact with the substrate, a HTL in contact with the anode layer, an ETL in contact with the HTL, and an electrode injecting cathode layer in contact with the ETL. If the cathode layer is a metal cathode layer of Mg:Ag, then a metal protective layer, for example, made of a layer of Ag for protecting the Mg:Ag cathode layer from atmospheric oxidation, may also be present.

The heterostructure for producing electro-luminescence may also include a protection layer and/or an injection enhancement layer between the anode layer and the HTL or the cathode layer and the ETL. The protection layer serves to protect the underlying organic layers from damage during deposition of an ITO layer, for example. An injection enhancement layer serves to enhance injection of holes from the anode into the adjacent HTL, such as disclosed in Ser. No. 08/865,491, now U.S. Pat. No. 5,998,803, for example, or to enhance injection of electrons from the cathode into the adjacent ETL, such as disclosed in copending Ser. No. 08/964,863, for example.

If a double heterostructure is used to produce electro-luminescence, a separate emissive layer is included between the HTL and the ETL. The term "emissive layer" as used herein may refer either to the emissive electron transporting layer or emissive hole transporting layer of a single heterostructure or the separate emissive layer of a double heterostructure. The emissive layer of a double heterostructure is referred to as a "separate" emissive layer so as to distinguish it from the ETL of a single heterostructure, which may also be an emissive layer. The materials, methods and apparatus for preparing the organic thin films of a single or double heterostructure are disclosed, for example, in U.S. Pat. No. 5,554,220, which is incorporated herein in its entirety by reference.

Alternatively, the heterostructure for producing electro-luminescence may have an inverted (IOLED) structure in which the sequence of layers deposited on the substrate is inverted, that is, an electron injecting cathode layer is in direct contact with the substrate, an electron transporting layer is in contact with the cathode layer, a hole transporting layer is in contact with the electron transporting layer, and a hole injecting anode layer is in contact with the hole transporting layer.

If the heterostructure for producing electro-luminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al).

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

In addition to the materials as disclosed herein for use in the HTL or in the ETL, other materials that may be used in the HTL in a representative embodiment of the present invention include, in particular, N,N'-diphenyl-N,N'-bis(3-methylphenyl)1-1'biphenyl-4,4'diamine (TPD), 4,4'-bis[N-(1-naphthyl)-N-phenyl-amino]biphenyl ($\alpha$-NPD) or 4,4'-bis [N-(2-naphthyl)-N-phenyl-amino]biphenyl ($\beta$-NPD). Other materials that may be used as the ETL include, in particular, aluminum tris(8-hydroxyquinolate) ($Alq_3$), a carbazole, an oxadiazole, a triazole, a thiophene or oligothiophene group. Other materials that may be used as the separate emissive layer, if present, include, in particular, dye-doped $Alq_3$, or substantially any other material that may be used as the separate emissive layer of an OLED.

Materials that may be used as the electron-injecting, metal cathode layer in a representative embodiment of the present invention include, in particular, Mg—Ag, Li—Ag or Ca, or a non-metallic material such as ITO, such as disclosed in copending Ser. No. 08/964,863, or substantially any other material that may be used as the cathode layer of an OLED.

The insulating layer, if present, may be comprised of an insulating material such as $SiO_2$, SiN, or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as 10μ, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the metal cathode layer from about 50 Å to greater than about 100 Å thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED has a charge carrier layer that includes a compound having molecules having at least one electron transporting moiety and at least one hole transporting moiety. More specifically, the molecule having at least one electron transporting moiety and at least one hole transporting moiety is comprised of a 2-methyl-8-quinolinolato ligand coordinated with a metal selected from the group consisting of Al, Ga, and In, as the electron transporting moiety.

The subject invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996), now U.S. Pat. No. 6,046,543; "Novel Materials for Multicolor LED's", Ser. No. 08/850,264 (filed May 2, 1997), now U.S. Pat. No. 6,045,930; "Electron Transporting and Light Emitting Layers Based on Organic Free Radicals", Ser. No. 08/774,120 (filed Dec. 23, 1996), U.S. Pat. No. 5,811,833; "Multicolor Display Devices", Ser. No. 08/772,333 (filed Dec. 23, 1996), U.S. Pat. No. 6,013,982; "Red-Emitting Organic Light Emitting Devices (LED's)", Ser. No. 08/774,087 (filed Dec. 23, 1996), now U.S. Pat. No. 6,048,630; "Driving Circuit For Stacked Organic Light Emitting Devices", Ser. No. 08/792,050 (filed Feb. 3, 1997), now U.S. Pat. No. 5,757,139; "High Efficiency Organic Light Emitting Device Structures", Ser. No. 08/772,332 (filed Dec. 23, 1996), now U.S. Pat. No. 5,834,893; "Vacuum Deposited, Non-Polymeric Flexible Organic Light Emitting Devices", Ser. No. 08/789,319 (filed Jan. 23, 1997), now U.S. Pat. No. 5,844,363; "Displays Having Mesa Pixel Configuration", Ser. No. 08/794,595 (filed Feb. 3, 1997), now U.S. Pat. No. 6,091,195; "Stacked Organic Light Emitting Devices", Ser. No. 08/792,046 (filed Feb. 3, 1997), now U.S. Pat. No. 5,917,280; "High Contrast Transparent Organic Light Emitting Device Display", Ser. No. 08/821,380 (filed Mar. 20, 1997), now U.S. Pat. No. 5,986,401; "Organic Light Emitting Devices Containing A Metal Complex of 5-Hydroxy-Quinoxaline as A Host Material", Ser. No. 08/838,099 (filed Apr. 15, 1997), now U.S. Pat. No. 5,861,219; "Light Emitting Devices Having High Brightness", Ser. No. 08/844,353 (filed Apr. 18, 1997), now U.S. Pat. No. 6,125,226; "Organic Semiconductor Laser", Ser. No. 60/046,061 (filed May 9, 1997), expired; "Organic Semiconductor Laser", Ser. No. 08/859,468 (filed May 19, 1997), now U.S. Pat. No. 6,111,902; "Saturated Full Color Stacked Organic Light Emitting Devices", Ser. No. 08/858,994 (filed May 20, 1997), now U.S. Pat. No. 5,932,895; "An Organic Light Emitting Device Containing a Hole Injection Enhancement Layer", Ser. No. 08/865,491 (filed May 29, 1997), now U.S. Pat. No. 5,998,803; "Plasma Treatment of Conductive Layers", Ser. No. PCT/US97/10252; (filed Jun. 12, 1997); Patterning of Thin Films for the Fabrication of Organic Multi-Color Displays", Ser. No. PCT/US97/10289 (filed Jun. 12, 1997); "Double Heterostructure Infrared and Vertical Cavity Surface Emitting Organic Lasers", Ser. No. 60/053,176 (filed Jul. 18, 1997), expired; "Oleds Containing Thermally Stable Asymmetric Charge Carrier Materials", Ser. No. 08/925,029 filed (Sep. 8, 1997), now U.S. Pat. No. 6,242,115; "Light Emitting Device with Stack of Oleds and Phosphor Downconverter", Ser. No. 08/925,403 (filed Sep. 9, 1997), now U.S. Pat. No. 5,874,803, "An Improved Method for Depositing Indium Tin Oxide Layers in Organic Light Emitting Devices", Ser. No. 08/928,800 (filed Sep. 12, 1997), now U.S. Pat. No. 5,981,306, "Azlactone-Related Dopants in the Emissive Layer of an Oled" (filed Oct. 9, 1997), Ser. No. 08/948,130, now U.S. Pat. No. 6,030,715 "A Highly Transparent Organic Light Emitting Device Employing A Non-Metallic Cathode", (filed Nov. 3, 1997), Ser. No. 60/064,005 (Provisional), expired, "A Highly Transparent Organic Light Emitting Device Employing a Non-Metallic Cathode", (filed Nov. 5, 1997), Ser. No. 08/964,863, "Low Pressure Vapor Phase Deposition of Organic Thin Films" (filed Nov. 17, 1997), Ser. No. 08/972,156, "Method of Fabricating and Patterning Oleds", (filed Nov. 24, 1997), Ser. No. 08/977,205, now U.S. Pat. No. 6,013,538, "Method for Deposition and Patterning of Organic Thin Film", (filed Nov. 24, 1997), Ser. No. 08/976,666, now U.S. Pat. No. 5,953,587, "Oleds Doped with Phosphorescent Compounds", (filed Dec. 1, 1997), Ser. No. 08/980,986, now U.S. Pat. No. 6,303,238, "Organic Vertical-Cavity Surface-Emitting Laser Confirmation", (filed Jan. 22, 1998), Ser. No. 09/010,594, now U.S. Pat. No. 6,160,828, and "Electron Transporting and Light Emitting Layers Based on Organic Free Radicals", (filed Feb. 18, 1998), Ser. No. 09/025,660, now U.S. Pat. No. 5,922,396 each co-pending application being incorporated herein by reference in its entirety. The subject invention may also be used in conjunction with the subject matter of each of U.S. patent application Ser. Nos. 08/354,674, 08/613,207 and 08/632,322, now U.S. Pat. Nos. 5,707,745, 5,703,436 and 5,757,026 (respectively) 08/693,359 and provisional patent application Serial Nos. 60/010,013, expired, No. 60/024,001, expired, and 60/025,501, expired, each of which is also incorporated herein by reference in its entirety.

OLEDs of the present invention may be fabricated using the materials and structures as disclosed in these co-pending applications.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

Procedures for Fabrication of Organic Light-Emitting Devices (OLEDs)

Experimental:

UV-Visible spectra were measured on a Aviv Spectrophotometer, Model 14DS. H NMR spectra were recorded on a Bruker 250 spectrometer. Photo- and electroluminescent spectra were measured with a Photon Technology International fluorimeter. Current-Voltage characteristics measurements were recorded on an EG&G Instruments Potentiostat, model 283. Melting point was measured on a Mel-Temp II device without calibration. Elemental analysis was performed by the Atlantic Microlab, Inc. Mass spectroscopic analysis was performed on a solid state probe of a Hewlett-Packard GC/MS spectrometer with a 5973 Mass Selective Detector. Gradient sublimation was conducted on a Lindberg three-zone oven with a base vacuum of $10^{-3}$ torr.

Chemicals:

Compounds that include a series of phenol derivatives bearing a triarylamine moiety which is known to have good hole transporting properties were further reacted with $Al(OPr)_3$ in the presence of two equivalents of 8-hydroxyquinaldine to create compounds bearing both electron transporting moiety and hole transporting moiety. The compounds so created are referred to as Al-pNP, Al-pCb, and Al-mCb.

TPD and $Alq_3$ were synthesized according to literature procedure, and both were sublimed before use. The ligands 4-(N-phenyl-2-naphthylamino)phenol, 3-carbazolphenol, 4-carbazolphenol, and 4-iminostilbenephenol were synthesized using the Ullman coupling of the iodoanisoles with the corresponding amines followed by deprotection of the methoxy group with $BBr_3$ as described in "Oleds Containing Thermally Stable Asymmetric Charge Carrier Materials", Ser. No. 08/925,029, filed Sep. 8, 1997, now U.S. Pat. No. 6,242,115, which is incorporated herein by reference. 8-hydroxyquinaldine was purchased from Aldrich and used as received.

Bis(2-methyl-8-quinolinolato)[p-(N-phenyl-2-naphthylamino)phenolato]aluminum(III), Al-pNP: To the mixture of $Al(OPr)_3$ (0.63 g, 3.1 mmol) and 8-hydroxyquinaldine (0.51 g, 3.2 mmol) were added 40 mL EtOH under argon. The mixture was refluxed for 3 hours to give a green-yellow solution. An orange-yellow solution of 8-hydroxyquinaldine (0.51 g, 3.2 mmol) and p-(N-phenyl-2-naphthylamino)phenol (1.45 g, 4.68 mmol) in 40 mL EtOH was then added in the air. The mixture was refluxed overnight. Solvent was then removed from the yellow solution and the yellow glassy material was then sublimed at over 300° C. The latest sublimed yellow crystalline material was collected and resublimed. An analysis of the resultant material gave the following results:

Yield: 60%; Melting Point: 136–142° C.; Elemental Composition (calculated): C, 77.2; H, 4.93; N, 6.43; Elemental Composition (measured): C, 77.0; H, 5.00; N, 6.31; Mass Spectroscopy: 653 (p), 342 (p-p-(N-phenyl-2-napthylamino)phenol), 259 (p-(N-phenyl-2-napthylamino)phenol), 159 (8-hydroxyquinaldine).

Bis(2-methyl-8-quinolinolato)(p-carbazolphenolato) aluminum(III), Al-pCb: To the mixture of $Al(OPr)_3$ (0.63 g, 3.1 mmol) and 8-hydroxyquinaldine (0.51 g, 3.2 mmol) were added 40 mL EtOH under argon. The mixture was refluxed for 3 hours to give a green-yellow solution. An orange-yellow solution of 8-hydroxyquinaldine (0.51 g, 3.2 mmol) and p-carbazolphenol (1.2 g, 4.6 mmol) in 40 mL EtOH was then added in the air. The mixture was refluxed overnight. Solvent was then removed from the yellow solution and the yellow glassy material was then sublimed at over 300° C. The latest sublimed yellow crystalline material was collected and resublimed. An analysis of the resultant material gave the following results:

Yield: 63%; Melting Point: 283° C.; Elemental Composition (calculated): C, 75.9; H, 4.69; N, 6.98; Elemental Composition (measured): C, 75.6; H, 4.79; N, 6.96; Mass Spectroscopy: 601 (p), 343 (p-p-carbazolphenolato), 259 (p-carbazolphenol), 159 (8-hydroxyquinaldine).

Bis(2-methyl-8-quinolinolato)(m-carbazolphenolato) aluminum(III), Al-mCb: $Al(OPr)_3$ (0.28 g. 1.37 mmol) was mixed with 8-hydroxyquinaldine (0.22 g, 1.38 mmol) in ethanol (65 mL) under argon. The mixture was refluxed under Ar for 2 hours, and the resulting yellow-green solution was filtered in the air through celite to give a clear solution. An ethanol solution (30 mL) of 2-methyl-8-quinoline (0.22 g, 1.38 mmol) and meta-carbazolphenol (0.54 g, 2.1 mmol) was added and the combined yellow-green solution was refluxed for 3 hours. Volatile materials were then removed under reduced vacuum and the glassy material was sublimed twice at 280° C. through a 3-zone sublimator to give a light yellow microcrystalline solid. An analysis of the resultant material gave the following results:

Yield: 0.29 g (35%); Melting Point: 280° C.; Elemental Composition (calculated): C, 75.9; H, 4.69; N, 6.98; Elemental Composition (measured): $C_3$ 75.1; H, 4.72; N 6.90; Mass Spectroscopy: 601 (p), 343 (p-m-carbazolphenolato), 259 (m-carbazolphenol), 159 (8-hydroxyquinaldine).

Device Fabrication and Characterization:

Borosilicate substrates coated with ITO (100 $\Omega/\square$) were cleaned by sonicating with detergent for five minutes followed by rinsing with deionized water. They were treated twice in boiling 1,1,1-trichloroethane for two minutes. The substrates were then sonicated twice with acetone for two minutes, twice with methanol for two minutes, and dried under $N_2$ flow.

The background pressure in the deposition system prior to device fabrication was normally $7\times10^{-7}$ torr or lower and the pressure during film deposition was between $5\times10^{-7}$ and $2\times10^{-6}$ torr. The compounds used for construction of the OLEDs were evaporated from restively heated tantalum boats onto the substrate held close to room temperature. TPD was first deposited at a rate from 1 to 4 Å/s to give a 300 Å film, followed by a layer of the electron transporting layer ($Alq_3$, $Alx_3$) deposited at a rate of 1 to 40 Å/s to a thickness of 450 Å. For dye doped OLEDs the electron transporting material and dye were co-deposited at the desired ratio.

The chamber was vented to air and shadow masks were put directly onto the substrates. Magnesium and silver were then co-deposited at a rate normally of 3 Å/s. The ratio of Mg:Ag varied from 7:1 to 12:1. The thickness of this layer was typically 500 Å. Finally, the devices were capped with 1000 Å Ag at a deposition rate between 1 to 4 Å/s.

Three types of OLEDs were fabricated having molecules having at least one electron transporting moiety and at least one hole transporting moiety:

Type SH-A: ITO\TPD (300 Å)\HET\Mg—Ag (500 Å)\Ag (1000 Å)

Type SH-B ITO\HET\Alq$_3$ (450 Å)\Mg—Ag (500 Å)\Ag (1000 Å)

Type DH: ITO\TPD (300 Å)\HET\Alq$_3$\Mg—Ag (500 Å)\Ag (1000 Å)

where HET represents a charge carrier layer that includes a compound having molecules having at least one electron transporting moiety and at least one hole transporting moiety, such as Al-pNP or Al-pCb. In addition, a TPD/Alq$_3$ OLED was typically fabricated at the same time as the OLEDs of type SH-A, SH-B and DH, for use as a reference. The devices were characterized in air within five hours of fabrication.

Experimental Results:

Each of the OLEDs fabricated had a heterostructure which had a charge carrier layer that included a compound having molecules having at least one electron transporting moiety and at least one hole transporting moiety, which was also an emissive material.

The absorption and photo-luminescent (PL) spectra of Al-pNP, Al-pCb, and Al-mCb in solution in CH$_2$Cl$_2$ are shown in FIG. 1. All three compounds show absorption at between 280 and 380 nm. The carbazole derivatives Al-pCb and Al-mCb show strong blue emission at around 360 nm, and Al-pCb has a lower energy emission at 480 nm. Al-pNP shows a single strong blue emission at around 440 nm which indicates the potential application of this material as a blue emitter.

In order to probe the properties of these new materials, different types of OLEDs were fabricated with the Al-pNP and Al-pCb. As described above, three types of OLEDs were fabricated for each material, type SH-A, SH-B and DH. Films of TPD and Al-pCb were also deposited onto a substrate. These films were pumped using ultraviolet radiation, and the absorption and PL emission were measured.

Figure 2:
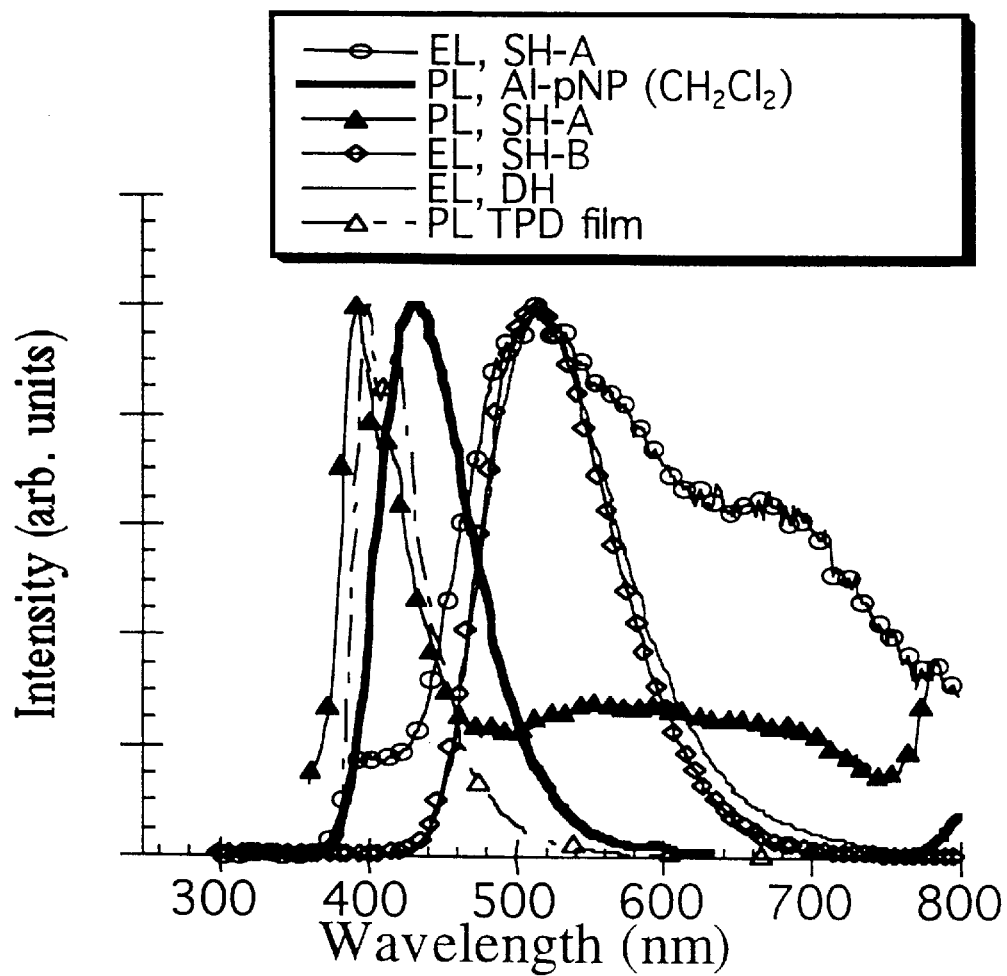
FIG. 2 shows electro-luminescent (EL) and photo-luminescent (PL) spectra of OLEDs having an Al-pNP layer.
Figure 3:
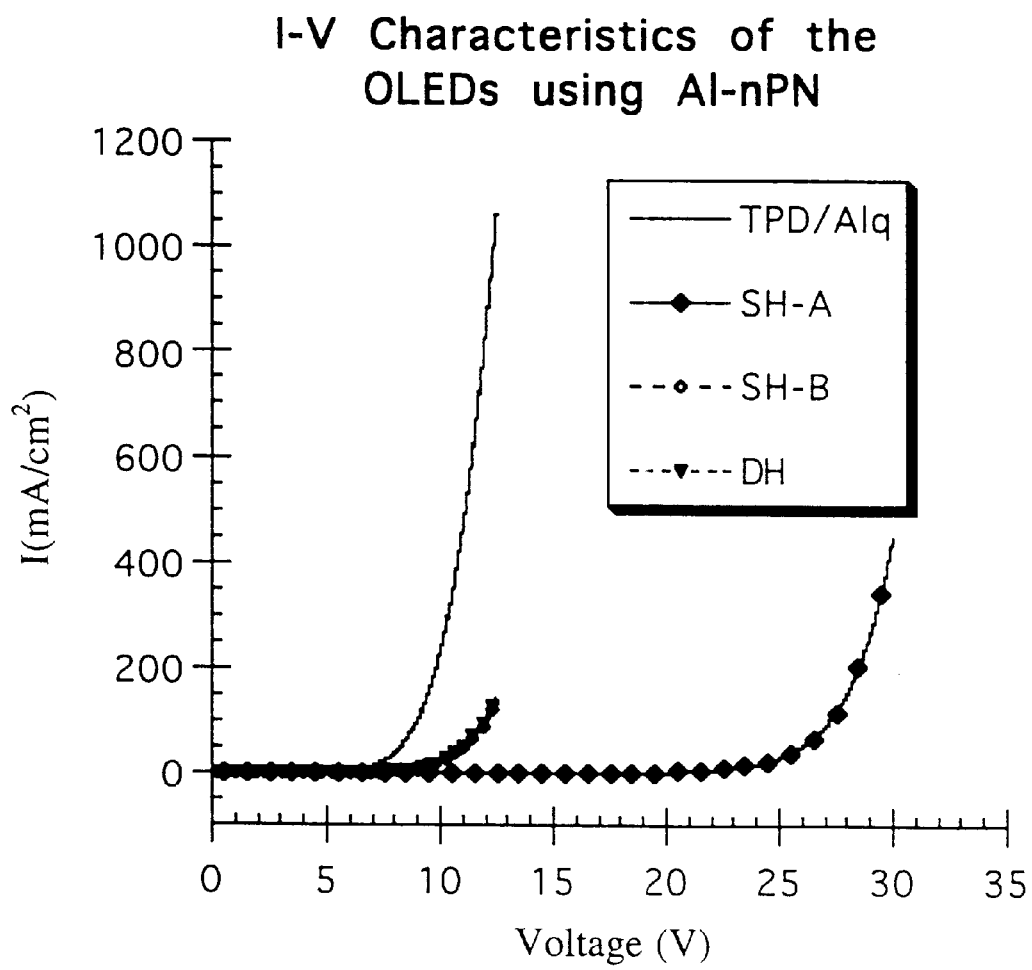
FIG. 3 shows I-V characteristics of OLEDs having an Al-pNP layer.

FIG. 2 shows the electro-luminescent (EL) spectra of OLEDs of type SH-A, SH-B, and DH fabricated with Al-pNP, and the PL spectra of an OLED of type SH-A, Al-pNP in CH$_2$Cl$_2$, and a TPD film. FIG. 3 shows the I-V characteristics of OLEDs of type SH-A, SH-B and DH fabricated with Al-pNP, as well as a reference OLED having a TPD HTL and an Alq$_3$ ETL. Table 1 summarizes the yield, PL, and EL data for the OLEDs fabricated with Al-pNP. In FIGS. 2 and 3 and Table 1, "SH-A" refers to a single heterostructure OLED having a TPD HTL and an Al-pNP ETL (300 Å TPD/1000 Å Al-pNP). "SH-B" refers to a single heterostructure OLED having an Al-pNP HTL and an Alq$_3$ ETL (300 Å Al-pNP/450 Å Alq$_3$). "DH" refers to a double heterostructure OLED having a TPD HTL, an Al-pNP seperate emissive layer, and an Alq$_3$ ETL (300 Å TPD/200 Å Al-pNP/450 Å Alq3). The "reference yield" row of Table 1 refers to the yield of a reference SH OLED with a TPD HTL and an Alq$_3$ ETL (300 Å TPD/450 Å Alq$_3$) fabricated at the same time as the OLED at the top of the column. The maximums reported in Table 1 are maximums in the visible range, and may be broad maximums that do not correspond to the highest peak of FIG. 2.

As shown in Table 1, the SH-A OLED with Al-pNP is inefficient, having a low yield of 0.0005%, although the low yield may be explained to some extent by contamination, which is indicated by the low reference yield of the reference OLED. The SH-A OLED with Al-pNP emits white light. The SH-B OLED with Al-pNP has a better yield of 0.02%. The DH OLED with Al-pNP has an even better yield of 0.05% and improved I-V characteristics, as illustrated in FIG. 3.

These results indicate that Al-pNP has some hole-transporting properties but is a poor emitter in the solid.

TABLE 1

| Structure | SH-A | SH-B | DH |
| --- | --- | --- | --- |
| Yield (%) | 0.0005 | 0.02 | 0.05 |
| Yield (%) (reference) | 0.02 | 0.1 | 0.1 |
| PL (nm) | 565 | 519 | 518 |
| EL (nm) | 525 | 514 | 520 |

Figure 4:
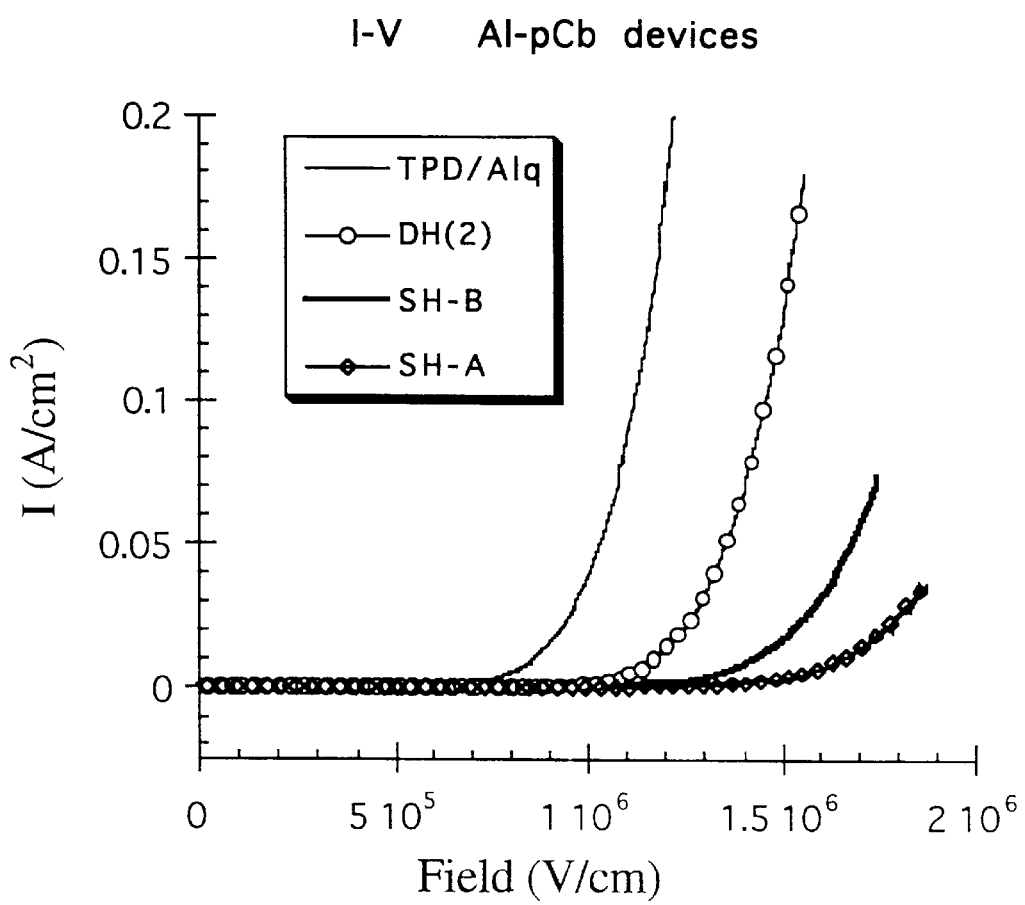
FIG. 4 shows EL and PL spectra of OLEDs having an Al-pCb layer.
Figure 5:
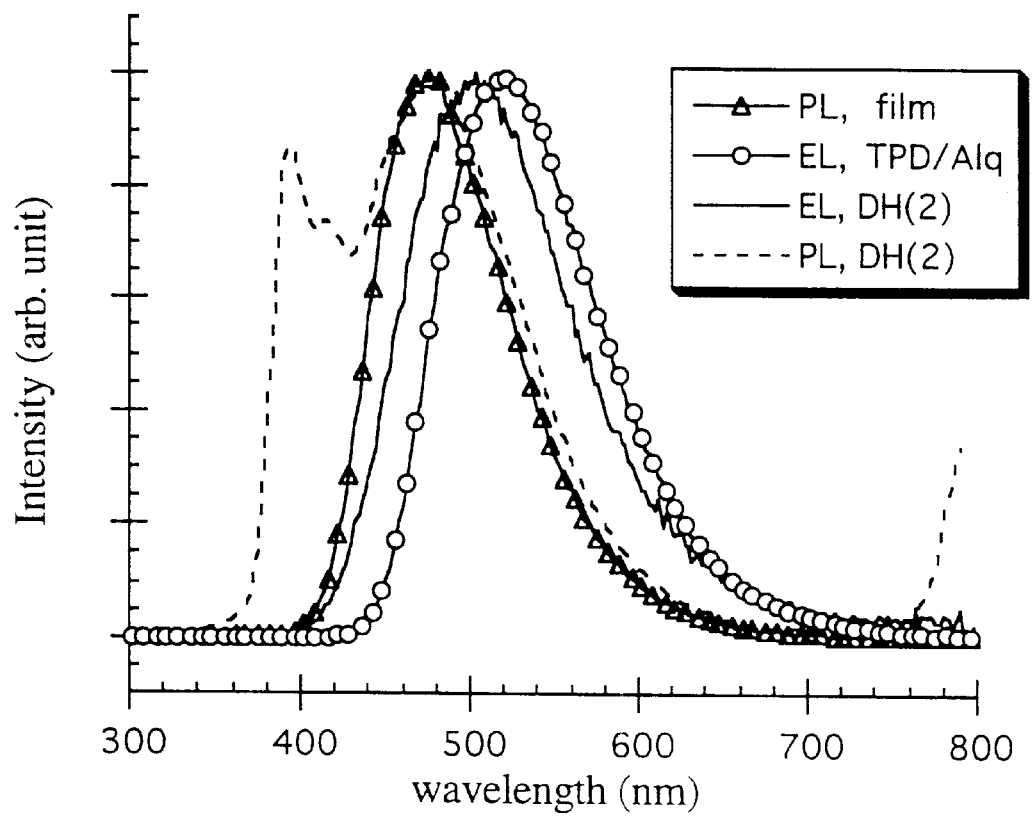
FIG. 5 shows I-V characteristics of OLEDs having an Al-pCb layer.

FIG. 4 shows the I-V characteristics of OLEDs of type SH-A, SH-B and DH(2) fabricated with Al-pCb, as well as a reference OLED having a TPD HTL and an Alq$_3$ ETL. FIG. 5 shows the EL spectra of an OLED of type DH(2) and a reference OLED, and the PL spectra of an OLED of type DH(2) and a film of Al-pCb. Table 2 summarizes yield, PL, and EL data for OLEDs fabricated with Al-pCb. In FIGS. 4 and 5 and Table 2, "SH-A" refers to a single heterostructure OLED having a TPD HTL and an Al-pCb ETL (300 Å TPD/500 Å Al-pCb). "SH-B" refers to a single heterostructure OLED having an Al-pCb HTL and an Alq$_3$ ETL (300 Å Al-pCb/450 Å Alq$_3$). "DH(1)" refers to a double heterostructure OLED having a TPD HTL, an Al-pCb separate emissive layer, and an Alq$_3$ ETL (300 Å TPD/450 Å Al-pCb/450 Å Alq$_3$). "DH(2)" refers to a double heterostructure OLED having the same materials as DH(1), but deposited to different thicknesses (300 Å TPD/410 Å Al-pCb/40 Å Alq$_3$). The "reference yield" row of Table 2 refers to the yield of a reference SH OLED with a TPD HTL and an Alq$_3$ ETL (300 Å TPD/450 Å Alq$_3$) fabricated at the same time as the OLED at the top of the column.

The application of Al-pCb in OLEDs of types SH-A, SH-B and DH led to results better than those for Al-pNP both in terms of color and efficiency. The PL spectra of the Al-pCb film, as shown in FIG. 5, is similar to that of Al-pCb in a CH$_2$Cl$_2$ solution, as shown in FIG. 1, having the same blue emission, and had an intensity comparable to that of Alq$_3$. As shown in FIG. 5 and Table 2, the DH(2) OLED with Al-pCb has a blue emission with a peak at about 500 nm.

TABLE 2

| Structure | SH-A | SH-B | DH (1) | DH (2) |
| --- | --- | --- | --- | --- |
| Yield (%) | 0.03 | 0.001 | 0.11 | 0.02 |
| Yield (%) (reference) | 0.14 | 0.14 | 0.14 | 0.14 |
| PL (nm) | 480 | 509 | 495 | 480 |
| EL (nm) | 500 | 518 | 518 | 500 |

Figure 6:
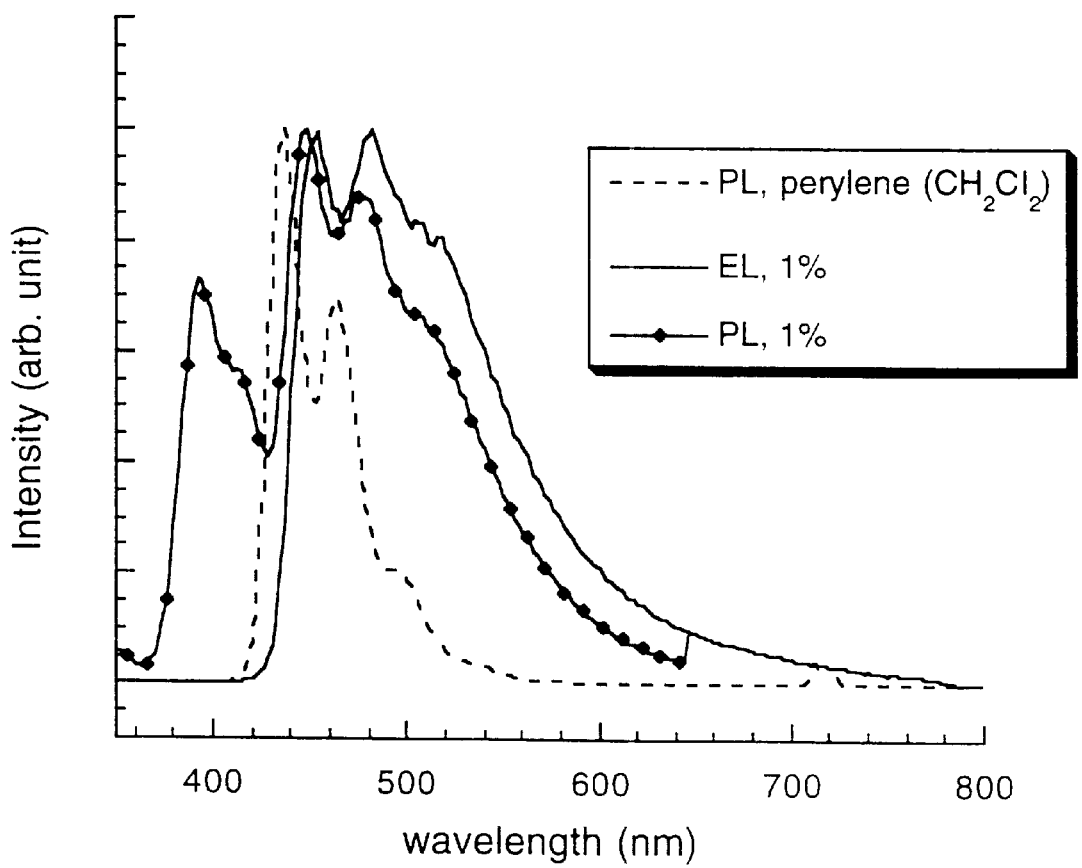
FIG. 6 shows EL and PL spectra of OLEDs having an Al-pCb/perylene layer.
Figure 7:
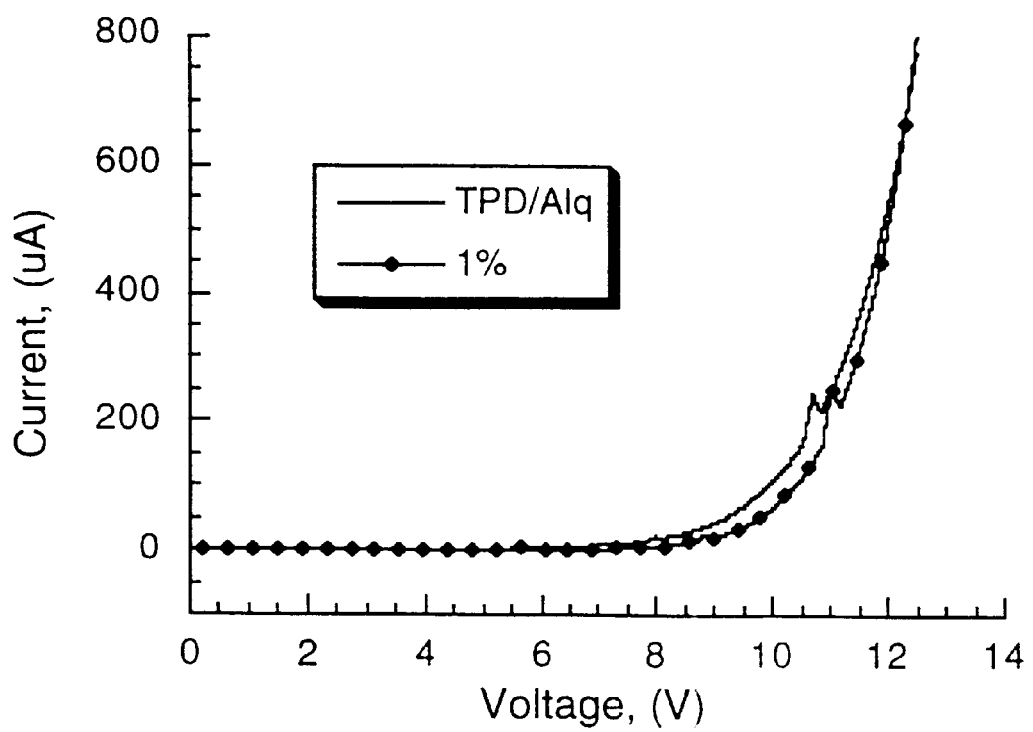
FIG. 7 shows I-V characteristics of OLEDs having an Al-pCb/perylene layer.

The efficiency and color purity of the DH(2) OLED with Al-pCb was further improved by the dye-doping technique. FIG. 6 shows the PL spectra of perylene in a CH$_2$Cl$_2$ solution and a DH(2) OLED with Al-pCb, uniformly doped with 1% perylene, and the EL spectrum of the same OLED. FIG. 7 shows the I-V characteristics of a DH(2) OLED with Al-pCb, uniformly doped with 1% perylene, and a TPD/Alq$_3$ OLED where the Alq$_3$ is doped with 1% perylene. Table 3 shows the yield, PL and EL data for OLEDs fabricated with Al-pCb. In FIGS. 6 and 7 and Table 3, "DH(2)" refers to a double heterostructure OLED having a TPD HTL, a layer of Al-pCb uniformly doped with 1% perylene as a seperate emissive layer, and a Alq$_3$ ETL (300 Å TPD/400 Å 1% perylene-Al-pCb/50 Å Alq$_3$). The "reference yield" row of Table 3 refers to the yield of a reference SH OLED with a TPD HTL and an Alq$_3$ ETL (300 Å TPD/450 Å Alq$_3$) fabricated at the same time as the OLED at the top of the column.

TABLE 3

| Structure | DH (2) |
|---|---|
| Yield (%) | 0.05 |
| Yield (%) (reference) | 0.12 |
| PL (nm) | 445 |
| EL (nm) | 455 |

When the Al-pCb layer was uniformly doped with 1 wt % perylene, the OLED had a more intense blue hue in its EL spectrum than when the Al-pCb layer was, not doped. The $\lambda_{max}$ (the wavelength having the greatest intensity) of the EL spectra of the doped device was characteristic of the $\lambda_{max}$ of the PL spectra of perylene in the solution, as shown in FIG. 6.

The quantum efficiency of the doped device was 2.5 times higher than that of the undoped one (0.05%). The EL spectrum of the doped device still had some tail to the green part of a spectrum due to the incomplete quenching of the host emission. This is indicative of some inefficiency in the energy transfer processes from the host to the dopant molecules.

The present invention may also be used with other blue dopants, such as coumarine 1, or dopants that emit other colors, such as green (i.e. coumarine 6) or red (i.e., 1,3-bis[4-(dimethylamino)-2-hydroxyphenyl]-2,4-dihydroxycyclobutenediylium dihydroxide).

Several embodiments of the present invention are specifically described and/or illustrated herein. However, it will be appreciated that modifications and variations of these embodiments are within the spirit and intended scope of the. present invention, and are within the purview of the appended claims.

What is claimed is:

1. An organic light emitting device comprising a heterostructure for producing electro-luminescence, wherein the heterostructure comprises a charge carrier layer wherein the charge carrier layer comprises a compound having two 2-methyl-8-quinolinolato ligands coordinated with Al as electron transporting moieties and one triarylamine derivatized phenoxide as a hole transporting moiety.

2. An organic light emitting device comprising a heterostructure for producing electro-luminescence, wherein the heterostructure comprises a charge carrier layer wherein the charge carrier layer comprises bis(2-methyl-8-quinolinolato)[p-(N-phenyl-2-naphthylamino)phenolato]aluminum(II).

3. An organic light emitting device, comprising a heterostructure for producing electro-luminescence, wherein the heterostructure comprises a charge carrier layer wherein the charge carrier layer comprises bis(2-methyl-8-quinolinolato)(p-carbazolphenolato)aluminum(III).

4. An organic light emitting device comprising a heterostructure for producing electro-luminescence, wherein the heterostructure comprises a charge carrier layer wherein the charge carrier layer comprises bis(2-methyl-8-quinolinolato)(m-carbazolphenolato)aluminum(III).

5. The organic light emitting device of claim 1 wherein said charge carrier layer is an emissive layer.

6. The organic light emitting device of claim 4, wherein said charge carrier layer is a separate emissive layer of a double heterostructure.

7. The organic light emitting device of claim 4 wherein said charge carrier layer is an electron transporting layer of a single heterostructure.

8. An organic light emitting device comprising a heterostructure for producing electro-luminescence, wherein the heterostructure comprises a charge carrier layer wherein the charge carrier layer comprises a compound having molecules having at least one electron transporting moiety, which is a 2-methyl-8-quinolinolato ligand coordinated with a metal selected from the group consisting of Al, Ga, and In, and at least one hole transporting moiety, wherein said charge carrier layer is an electron injector layer disposed between a cathode and an electron transporting layer.

9. The organic light emitting device of claim 1, wherein said charge carrier layer comprises said compound doped with a dye.

10. A display incorporating the organic light emitting device of claim 1.

11. A vehicle incorporating the organic light emitting device of claim 1.

12. A computer incorporating the organic light emitting device of claim 1.

13. A television incorporating the organic light emitting device of claim 1.

14. A printer incorporating the organic light emitting device of claim 1.

15. A wall, theater, or stadium screen incorporating the organic light emitting device of claim 1.

16. A billboard or a sign incorporating the organic light emitting device of claim 1.

17. A method of fabricating an organic light emitting device comprising: preparing a heterostructure for producing electro-luminescence, wherein the preparation process includes the step of forming a charge carrier layer, wherein the charge carrier layer comprises a compound having two 2-methyl-8 quinolinolato ligands coordinated with Al as electron transporting moieties and one triarylamine derivatized phenoxide as a hole transporting moiety.

* * * * *

UNITED STATES PATENT AND TRADEMARK OFFICE
CERTIFICATE OF CORRECTION

PATENT NO.    : 6,451,455 B1
DATED         : September 17, 2002
INVENTOR(S)   : Thompson et al.

It is certified that error appears in the above-identified patent and that said Letters Patent is hereby corrected as shown below:

Title page,
Item [56], OTHER PUBLICATIONS, the "D. Kim, et al." reference, change "Skelton" to -- Skeleton --;

Column 4,
Line 44, change "invention. (" to -- invention. -- ;

Column 15,
Line 13, change "was, not doped" to -- was not doped. -- ; and
Line 33, change "of the." to -- of the --.

Signed and Sealed this

Seventeenth Day of June, 2003

JAMES E. ROGAN
*Director of the United States Patent and Trademark Office*